US008679780B2

(12) United States Patent
Schmidt

(10) Patent No.: US 8,679,780 B2
(45) Date of Patent: Mar. 25, 2014

(54) METHOD OF REDUCING IMMUNOLOGICAL TOLERANCE TO MALIGNANCY

(76) Inventor: Geoffrey J. Schmidt, Norwell, MA (US)

( * ) Notice: Subject to any disclaimer, the term of this patent is extended or adjusted under 35 U.S.C. 154(b) by 1305 days.

(21) Appl. No.: 11/590,732

(22) Filed: Oct. 30, 2006

(65) Prior Publication Data
US 2007/0053893 A1 Mar. 8, 2007

Related U.S. Application Data

(62) Division of application No. 08/856,867, filed on May 15, 1997, now abandoned.

(51) Int. Cl.
*C12P 21/06* (2006.01)
(52) U.S. Cl.
USPC .......................................... 435/69.1
(58) Field of Classification Search
None
See application file for complete search history.

(56) References Cited

U.S. PATENT DOCUMENTS

| | | | |
|---|---|---|---|
| 5,079,230 A | | 1/1992 | Randawa et al. |
| 5,100,661 A | * | 3/1992 | Schmidt ..................... 424/146.1 |

OTHER PUBLICATIONS

Gowada et al. A Novel Inhibitor Protein of N-Myristoyltransferase From *Esherichia coli*. Biochemical and Biophysical Research Comm. vol. 314, pp. 984-987. 2004.*
Shrivastav et al. "Regulation of N-Myristoyltransferase by Novel Inhibitor Proteins." Cell Biochemistry and Biophysics. vol. 43, pp. 189-202. 2005.*
Selvakumar et al. "Potential role of N-myristoyltransferase in cancer." Progress in Lipid Research, 46, pp. 1-36 (2007).*
Schmidt et al. (1983) Invest. Opthalmol. Vis. Sci. 24:244.
Cockcroft (1987) Trends Biochem. 12:75-78.
Dizhoor et al. (1992) J. Biol. Chem. 267:16033-16036.
Thirkill et al. (1993) Arch. Ophthalmol. 111:974-976.
Schmidt et al. (1988) Invest. Ophthalmol. Vis. Sci. 28:94.
Schmidt et al. (1989) Invest. Ophthalmol. Vis. Sci. 30: 172.
Whitman et al. (1986) Phospohoinsitides and Receptor Mechanisms, (Alan R. Liss, Inc.) pp. 197-217.
Thirkill et al. (1992) Invest. Ophthalmol. Vis. Sci. 33:2768-2772.
Gery et al. (1994) Invest. Ophthalmol. Vis. Sci. 34:3342-3345.
Abbas et al. (1991) Cellular and Molecular Immunology (B. Saunders Co., Philadelphia, PA) pp. 335-332.
Olsen et al. (1985) J. Biol. Chem. 260:3784-3790.
Magnuson et al. (1995) J. Natl. Cancer Inst. 87:1630-1635.

* cited by examiner

*Primary Examiner* — Marcela M Cordero Garcia
*Assistant Examiner* — Kaipeen Yang
(74) *Attorney, Agent, or Firm* — Novak Druce Connolly Bove + Quigg LLP

(57) ABSTRACT

Disclosed are therapeutic formulations comprising myristoylCoA and N-myristoyl transferase and methods of using such formulations to stimulate the immune system of a mammal afflicted with carcinoma and having a detectable blood level of unacylated A-protein to produce an immune response thereto. Also disclosed are methods of treating an A-protein displaying carcinoma in a mammal.

6 Claims, 2 Drawing Sheets

SEQUENCE LISTING

<160> NUMBER OF SEQ ID NOS: 2

<210> SEQ ID NO 1
<211> LENGTH: 50
<212> TYPE: DNA
<213> ORGANISM: Unknown
<220> FEATURE:
<223> OTHER INFORMATION: Yeast
<220> FEATURE:
<221> NAME/KEY: DNA
<222> LOCATION: (1)..(50)

<400> SEQUENCE: 1
cggtagtaaa cggatccata ccatggcaga agaggataaa gcgaaaaaat          50

<210> SEQ ID NO 2
<211> LENGTH: 5
<212> TYPE: PRT
<213> ORGANISM: Human
<220> FEATURE:
<221> NAME/KEY: peptide
<222> LOCATION: (1)..(5)

<400> SEQUENCE: 2

Gly Asn Ser Lys Ser
1               5

METHOD OF REDUCING IMMUNOLOGICAL TOLERANCE TO MALIGNANCY

Figure 1:
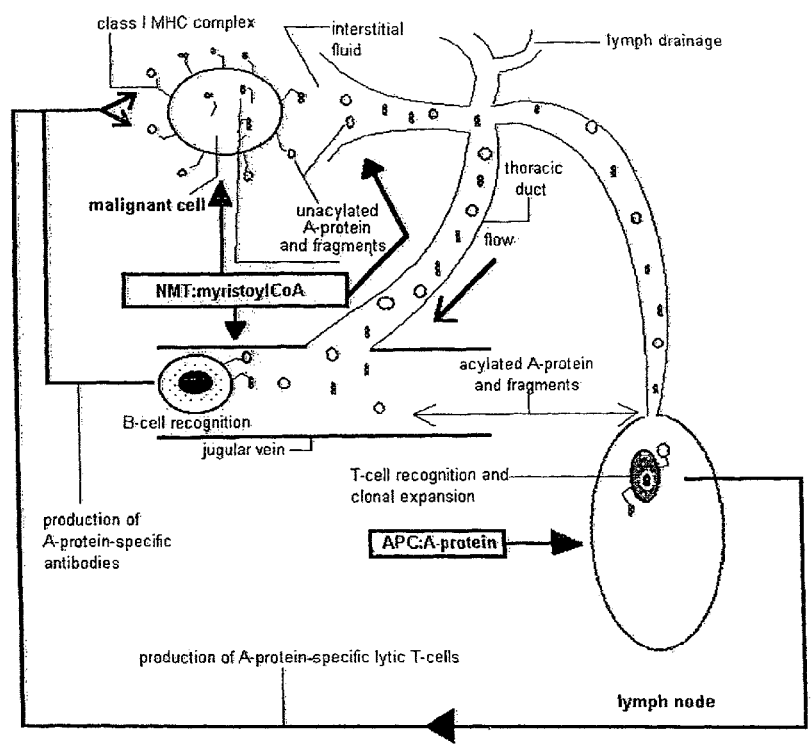
Figure 2:
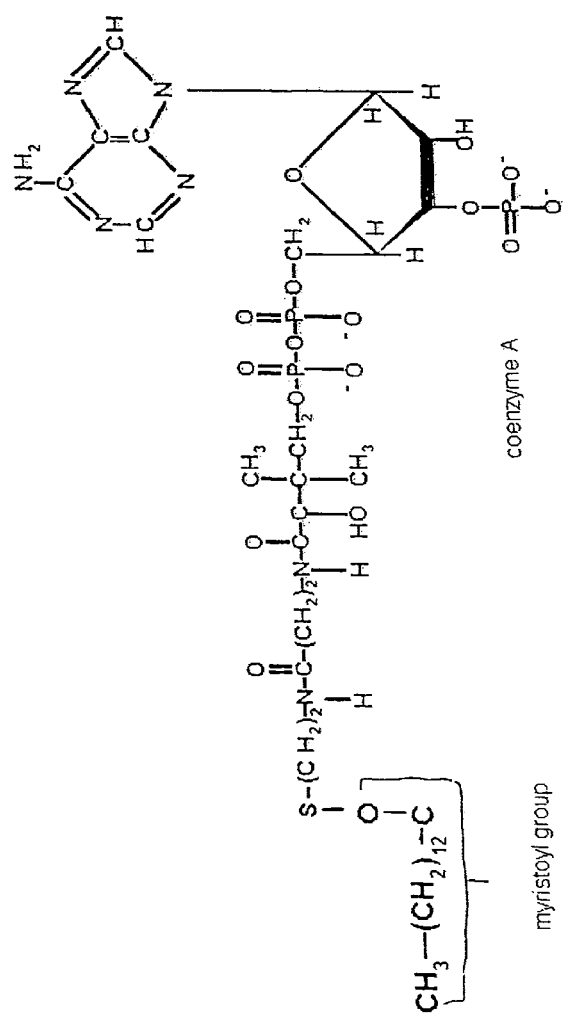

This application is a divisional of U.S. patent application Ser. No. 08/856,867, filed May 15, 1997, now abandoned the contents of which are incorporated herein by reference in their entirety.

BACKGROUND OF THE INVENTION

This invention relates to a method of treating cancer. More specifically, this invention relates to a mechanism by which tolerance of the body to malignant tissues is reduced using an immunosuppressant molecule, unacylated A-protein.

A-protein is a cellular enzyme that was first isolated from vertebrate rod photoreceptor cells in 1982 (Schmidt et al. (1983) *Invest. Ophthalmol. Vis. Sci.* 24:244). It has also been described in scientific literature under the names $G_P$ (Cockcroft (1987) *Trends Biochem. Sci.* 12:75-78), recoverin (Dizhoor et al. (1992) *J. Biol. Chem.* 267:16033-16036) and CAR protein (Thirkill et al. (1993) *Arch. Ophthalmol.* 111: 974-978). A-protein has been characterized as a GTP-binding protein (g-protein) (Schmidt et al. (1987) *Invest. Ophthalmol. Vis. Sci.* 28:94) that regulates phosphinositide metabolism by activating phospholipase C (Schmidt et al. (1988) *Invest Ophthalmol. Vis. Sci.* 29:123).

A-protein exists in two forms (Schmidt et al. (1989) *Invest. Ophthalmol. Vis. Sci.* 30:172; and Dizhoor et al. (1992) *J. Biol. Chem.* 267:16033-16036); as a monomer of 23,000 daltons which is soluble in the cytosol, and as a co-synthetically modified form to which a fatty acid is attached by the action of the enzyme N-myristoyl transferase (NMT; E.C.2.3.1.97) (Dizhoor et al. (1992) *J. Biol. Chem.* 267: 16033-16036). The modified form of A-protein tends to self-associate as stable pentameric homopolymers with an approximate molecular weight of 120,000 daltons which are peripherally bound on the inner aspect of the cell membrane.

In its peripherally membrane-bound form, A-protein is activated by a growth-factor receptor imbedded in the plasmalemma subsequent to activation of the receptor by a growth factor. The activation of this metabolic cascade mechanism results in a sustained release of calcium into the cytosol which ultimately stimulates the cell to divide. This general scheme is referred to as signal transduction (see U.S. Pat. No. 5,100, 661).

In non-ocular tissues, A-protein, by definition, transduces growth signals (Whitman et al. (1986) in *Phosphoinositides and Receptor Mechanisms* (Alan R. Liss, Inc.) pp. 197-217). The protein is expressed in mitotically active cells including malignant tissues. A-protein is expressed inside affected malignant cells and into the blood stream (Thirkill et al. (1993) *Arch. Ophthalmol.* 111:974-978). Fragments of the protein are also displayed on the surface of malignant cells (Thirkill et al. (1992) *Invest. Ophthalmol. Vis. Sci.* 33:2768-2772).

Gery et al. (*Invest. Ophthalmol. Vis. Sci.* (1994) 35:3342-3345) have demonstrated that A-protein is highly immunoreactive in a dose-dependent fashion in its myristoylated form when used to immunize rats. In contrast, the unmodified form of A-protein was ineffective in inducing antibody production in mice. In addition, booster immunization with the unmodified form of the protein could significantly diminish the titer of antibodies produced by mice immunized with the myristoylated form of A-protein.

It has been appreciated for some time that the immune system is a very specific mechanism for excision of neoplastic tissues (Abbas et al. in *Cellular and Molecular Immunology* (B. Saunders Co., Philadelphia, Pa.) (1991) pp. 335-352). However, the lack of immunogenicity of tumor cells has presented a stumbling block to the successful reactivation of the antitumor mechanisms of the immune system.

Thus, what is needed are methods of treating cancer which cause the immune system to regain the ability to recognize neoplastic tissue as an antigenic target and which recruit a directed autoimmune response to the tumor, thereby causing its regression.

SUMMARY OF THE INVENTION

The present invention provides therapeutic formulations and methods useful in resensitizing the immune system of a mammal afflicted with cancer to tumor cells. Such formulations and methods are also useful in preparing immune sera in healthy individuals which then can be used to treat carcinoma in cancer-tolerant subjects.

It is known that unacylated A-protein is expressed inside and on the surface of malignant cells such as small and large cell carcinoma of the lung and breast, prostate, colon, cervical and squamous cell carcinomas. It has been discovered that acylated A-protein can stimulate the immune system of a mammal afflicted with cancer and having a circulating level of detectable A-protein monomer to produce anti-A-protein antibodies. Acylation distinguishes the immunosuppressive (unacylated) form of A-protein from the immunogenic (acylated) form. This discovery has been exploited to develop the present invention.

In a first aspect, the invention provides a therapeutic composition which comprises myristoylCoA in a physiologically acceptable carrier and N-myristoyl transferase (NMT) in a physiologically acceptable carrier. As used herein, a "physiologically acceptable carrier" encompasses any and all solvents, dispersion media, coatings, antibacterial and antifungal agents, isotonic and absorption delaying agents and the like. The use of such media and agents for pharmaceutically active substances is well known in the art. In some embodiments, NMT is embedded in a stable biopolymer for slow release. As used herein, the term "biopolymer" encompasses—a biodegradable, implantable, polymeric, matrix which can contain a diffusible pharmacological agent. In particular embodiments, the slow release vehicle is a liposome.

In another aspect of the invention, a therapeutic composition is provided which comprises both myristoylCoA and NMT in a physiologically acceptable carrier. In some embodiments, NMT:myristoylCoA is embedded in a stable biopolymer for slow release. In some embodiments, the slow release vehicle is a liposome.

The invention also provides a method of treating either a primary or a metastatic tumor in a subject with a detectable blood level of unacylated, monomeric A-protein by relieving the tolerance of the immune system of the afflicted patient to the tumor.

As used herein, "primary tumor" refers to tumor growth at a first site and not secondary to growth elsewhere, while "metastatic tumor" refers to tumor growth at a site other than the original growth, caused by the migration of malignant cells from the first growth. In some embodiments, the method is used to treat a carcinoma such as small and large cell carcinoma of the lung, squamous cell, breast, colon and cervix.

"Unacylated A-protein" refers to unmodified monomers of A-protein having an apparent molecular weight on polyacrylamide gels of 23,000 daltons. The term "tolerance" is defined as a state of non-responsiveness to subsequent challenge with antigen, i.e., a tumor cell, by any of a variety of mechanisms, including, but not limited to, clonal deletion or apoptosis of antigen-specific T cells, prevention of appropriate presentation of the antigen by relevant antigen presenting cells, or induction of immune cells with suppressive, killer or anti-inflammatory capabilities, having specificity for the antigen itself or for the relevant antigen-specific T cells. "Relieving tolerance" is used herein as causing the immune system to recognize as foreign what was once considered as "self," hence enabling an immune response to be mounted.

In the method of the invention, a therapeutically effective amount of a pharmaceutical formulation comprising myristoylCoA and NMT is administered to the patient. In some embodiments, the formulation is administered systemically. In particular embodiments, the formulation is administered intravenously. The unacylated A-protein becomes acylated in the presence of the exogenous myristoylCoA and NMT thereby resensitizing the immune system of the patient to the tumor.

In accordance with the invention, a "therapeutically effective amount" of the therapeutic formulation is that amount of myristoylCoA and NMT which relieves the unacylated A-protein-induced suppression of the immune system's ability to recognize tumor cells as appropriate targets. When applied to an individual active ingredient (such as NMT or myristoylCoA), administered alone, the term refers to that ingredient alone. When applied to a combination, the term refers to combined amounts of the active ingredients that result in the therapeutic effect, whether administered in combination, serially, or simultaneously.

In another embodiment, the method of treating carcinoma described above is supplemented such that the immune system of the mammal afflicted with carcinoma but relieved of its tolerance thereto is stimulated to mount an immune response against the carcinoma. In this method, an immunologically active antigen presenting cell (APC) is isolated from a subject afflicted with cancer. The term "immunologically active antigen presenting cell" (APC) as used herein encompasses a cell which stimulates a clonal T-lymphocyte response by phagocytosing an immunologically active element and displays fragments or copies thereof on its surface in conjunction with major histocompatibility complex (MHC) proteins. In preferred embodiments, this APC is a dendritic cell, i.e., a bone marrow stem cell-derived, non-B-, non-T type leukocyte.

The APC is then contacted with at least an acylated peptide including the amino terminal amino acid sequence Gly-Asn-Ser-Lys-Ser ("GNSKS") (SEQ ID NO: 2), to which a myristoyl group is attached at the glycine residue, thereby sensitizing the APC to A-protein. In preferred embodiments, the APC is contacted with an acylated peptide having at least five amino acids including the amino terminal amino acid sequence Gly-Asn-Ser-Lys-Ser (SEQ ID NO: 2). In other embodiments, the APC is contacted with an acylated peptide having at least 10 amino acids including the amino terminal amino acid sequence Gly-Asn-Ser-Lys-Ser (SEQ ID NO: 2). In yet other embodiments, the APC is contacted with an acylated peptide having 10 to 14 amino acids including the amino terminal amino acid sequence Gly-Asn-Ser-Lys-Ser (SEQ ID NO: 2).

In another embodiment, the APC is contacted with a homopolymer of acylated A-protein. As used herein, the terms "acylated," "modified," "polymeric," "homopolymer," and "myristoylated" refer to A-protein or fragments thereof to which a myristoyl group (a 14 carbon fatty acid) has been attached. In some embodiments, the homopolymeric A-protein has been isolated from a mammalian species, such as bovine or human A-protein. In another embodiment, the A-protein homopolymer has been synthetically produced through recombinant or biochemical means and acylated by myristoyl transferase in vitro.

The sensitized APC is then administered to the patient, thereby stimulating the immune system of the subject to produce a T-cell-dependent response to the tumor which displays the same antigen, i.e., A-protein. In one preferred embodiment, administration is performed by intravenous injection.

In another aspect, the invention provides a method of treating a subject with carcinoma in which the immune system of a mammal afflicted with carcinoma is stimulated to mount an immune response to the carcinoma. In this method, an immunologically active antigen presenting cell (APC) as described above is isolated from a subject afflicted with cancer.

The APC is then contacted with at least an A-protein monomer or an unacylated peptide having at least the amino terminal amino acid sequence Gly-Asn-Ser-Lys-Ser (SEQ ID NO: 2), thereby sensitizing to A-protein. In preferred embodiments, the APC is contacted with an unacylated peptide having at least five amino acids including the amino terminal amino acid sequence Gly-Asn-Ser-Lys-Ser (SEQ ID NO: 2). In other embodiments, the APC is contacted with an unacylated peptide having at least 10 amino acids including-the amino terminal amino acid sequence Gly-Asn-Ser-Lys-Ser (SEQ ID NO: 2). In yet other embodiments, the APC is contacted with an unacylated peptide having 10 to 14 amino acids including the amino terminal amino acid sequence Gly-Asn-Ser-Lys-Ser (SEQ ID NO: 2).

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1 is a diagrammatic representation of the mechanism of action of the therapeutic formulation of the invention; and FIG. 2 is a schematic representation of myristoylated coenzyme A.

DETAILED DESCRIPTION OF THE PREFERRED EMBODIMENTS

The patent and scientific literature referred to herein establishes the knowledge that is available to those with skill in the art. The issued U.S. patents, allowed applications, published foreign applications, and references cited herein are hereby incorporated by reference.

The present invention provides therapeutic compositions including myristoylCoA and NMT, and further provides methods of treating cancer using such formulations, including methods of reducing tolerance of the body to malignant tissues and cells. The types of cancer which can be treated by this method include any carcinoma whose primary or metastatic tumor cells produce A-protein. Such carcinomas include, but not limited to, squamous cell, small and large cell carcinoma of the lung, and breast, colon, cervical, and prostate carcinomas.

Neither normal (non-cancerous) subjects nor most cancer patients have anti-A-protein antibodies in their system. However, human subjects who suffer from cancer-associated retinopathy (CAR), an autoimmune disease often correlated with small cell carcinoma of the lung (SCCL), have been shown to produce antibodies to endogenous A-protein (Thirkill et al. (1992) *Invest. Ophthalmol. Vis. Sci.* 33:2768-2772). It is likely that the normal induction of tolerance to A-protein elaborated by tumors seen in most cancer patients is not invoked in the autoimmune patients due to a generalized failure of the immune system of the ability to discriminate "self". Since the presence of antibodies against A-protein in these CAR patients does not prevent, clear, or control the disease, it is likely that antibodies against the modified form of A-protein do not recognize the unmodified form, and are thus ineffective in mounting and directing an immune response against the affected tissue. This indicates that the critical factor in recognition of A-protein is modification of A-protein by the addition of a 14-carbon fatty acid, i.e., a myristoyl group, (C 14:0), to A-protein. This addition is accomplished by NMT, for which A-protein is a specific substrate. (Dizhoor et al. (1992) *J. Biol. Chem.* 26.7:16033-16036; Olsen et al. (1985) *J. Biol. Chem.* 260:3784-3790). NMT binds a myristoyl group in the form of myristolylCoA, and links the fatty acid group via a hydrolysis-resistant amide linkage to the amino terminal glycine of proteins and peptides that have the appropriate adjacent amino acid motif.

The fact that the modified form of A-protein causes an immune reaction while the unmodified form induces tolerance suggests-a biological mechanism which communicates from tumor tissue to the immune system and vice versa. In one instance, the immune system is stimulated to produce antibodies which then target cells having A-protein fragments to which the antibodies bind. This antibody/antigen cell surface marker is the method by which cells are identified for destruction by T-lymphocytes and macrophages (Male et al. in *Immunology* (Roitt et al., eds.) Mosby, London (1993) sec. 1.3-1.4).

In another instance, the unmodified form of A-protein shown to be an immunosuppressant fulfills the same role in vivo and thus is partially or wholly responsible for the lack of immunogenicity of malignant cells. If the lack of cellular differentiation seen in cancer cells causes the partial or total loss of the ability of the cell to modify A-protein, (Olsen et al. (1985) *J. Biol. Chem.* 260:3784-3790), the change from immunoreactive, modified A-protein to immunosuppressant, unmodified A-protein correlates strongly with the earliest stages of tumor formation.

One regulatory pathway that is absent in cancer cells is the mechanism controlling cell division which is present in mature cells. This results in the overproduction of A-protein and an upset of the normal equilibrium between the monomer and the polymer, increasing the relative amount of monomer in the cytoplasm. At least one study (Magnuson et al. (1995) *J. Natl. Cancer Inst.* 87:1630-1635) has shown a substantial (six-fold) increase in NMT activity in transformed cells relative to normal. The increase is likely to be the result of the increased burden placed on the myristoylation pathway by A-protein, among others. It is unknown what the limiting factor is, although the availability of either NMT or myristoyl, a minor cellular constituent, are suspect.

Interestingly, the same study on NMT activity in humans (Magnuson et al., ibid.) found that there was not an increase in NMT activity in tissue affected by volvulus or Crohn's disease, implying that benign inflammatory disease or non-cancerous lesions do not cause the same cellular response.

The cell appears to be unable to meet the challenge of myristoylation at approximately the time that it becomes malignant. In addition, a substantial increase in NMT activity has been detected in precancerous lesions in rats and in human colon. The finding of increased NMT activity in cancer and precancer cells contrasts with other studies that indicate a sharp decline in the proportion of myristodylated substrate (Olsen et al. (1985) *J. Biol. Chem.* 260:3784-3790) in transformed cells. This indicates that these precursors of malignant tissues have already undergone an increase in substrate (A-protein, e.g.) production prior to clinical disease. The finding of a sharp increase in NMT activity prior to the establishment of the disease was repeated in rats.

The therapeutic formulation of the invention is useful for stimulating the immune system of a non-CAR carcinoma patient to recognize A-protein, a therapeutic composition is administered to the patient. In one form, this therapeutic composition comprises myristoylCoA in a physiologically acceptable carrier and NMT in physiologically acceptable carrier.

The preferred acyl substrate for NMT is myristoylCoA, a molecule that contains a myristoyl moiety linked to coenzyme (CoA) by a thioester bond. CoA is a required carrier for the acyl group. The preferred method of preparation of myristoylCoA is a modification of the methods of Hosaka (*Meth. Enzmol.* (1981) 71:325-333). Briefly, this entails incubation of the fatty acid with the enzyme acyl-CoA ligase, derived from commercially available *Pseudomonas* bacteria (Sigma Chemical Co., St. Louis, Mo.). Following the reaction, the mixture is titrated to pH 2 with HCl. Free fatty acid is removed by repeated extraction of the mixture with heptane. This extraction is generally done with equal proportions of the aqueous and organic phases. The myristoylCoA formed remains in the aqueous phase of the extraction.

NMT may be prepared from a mammalian or non-mammalian source, including, for example, yeast. Yeast NMT has been shown to have specificity for substrates that is nearly identical to that of mammalian forms of the protein (Duronio et al. (1992) *Proc. Natl. Acad. Sci.* (*USA*) 89:4129-4133), and is effective in tyristoylation of mammalian A-protein (Dizhoor et al. (1992) *J. Biol. Chem.* 267:16033-16036).

Yeast NMT may be prepared according to the methods of Towler et al. (*Proc. Natl. Acad. Sci.* (USA) (1987) 84:2708-2712; and *J. Biol. Chem.* (1987) 262:1030-1036). Briefly, 100 liters of yeast culture is grown aerobically at 30° C. in YPD (1% yeast extract, 2% Bacto-peptone, 2% glucose) in a fermentor. When the culture reaches an $OD_{660\,nm}$ of 4, an additional 2 kg is added to maintain exponential growth. Cells are harvested when the culture reaches an $OD_{660\,nm}$, of 8. Cells are broken with glass beads in a Biospec Bead Beater homogenizer (Biospec Products, Bartlesville, Okla.). The resulting crude lysate is made 51% saturated in ammonium sulfate and centrifuged at 4° C. for 1 hour at 12,500 rpm. The pellet is resuspended and the proteins are fractionated on an anion exchange column using a step-wise elution with 30 nM NaCl. Fractions containing NMT activity are pooled and rechromatographed on a column of CoA-agarose affinity matrix (Pharmacia P-L Biochemicals), eluted step-wise with an increasing concentration of potassium phosphate washes (10, 50, 100 and 200 mM).

Alternatively, the methods of Duronio et al. (*Proc. Natl. Acad. Sci.* (*USA*) (1990) 87:1506-1510) can be used to express yeast NMT gene-containing plasmids in *E. coli* by fermentation. A 780-base-pair (bp) region (nucleotides 213-993) of the 2.1 kilobase (kb) *BamHI-HindIII Saccharomyces cerevisiae* genomic NMT1 fragment is amplified using the polymerase chain reaction and a mutagenic oligonucleotide (5'-CGGTAGTAAACGGATCC-ATACCATG GCAGAAGAGGATAAĀGCḠAAAĀĀAT-3')(SEQ ID NO: 1). This allows the insertion of an Nco I restriction enzyme site at the initiator ATG codon of NMT1. The new Nco I site also changes codon two of NMT1 from a serine to an alanine encoding codon. The NCO I site allows linkage of the NMT1 gene to the *E. coli* recA promoter and a translational enhancer element (gene 10 leader). This is accomplished by ligating the newly generated 1.9 kb Nco I-HindIII fragment into plasmid. The resulting plasmid is then used to transform *E. coli*. The transformants are shaken at 37° C. in LB broth containing 100 μg of ampicillin per ml to an $OD_{600}$ of 1.0. The recA promoter is induced by adding nalidixic acid to a final concentration of 50 μg/ml. After a 15-20 minute incubation at 37° C., the cells are harvested by centrifugation and broken under pressure (2000 psi) with a french press. NMT is purified by sequential ammonium sulfate fractionation, anion exchange and COA-agarose affinity chromatography according to the methods of Towler et al. (*Proc. Natl. Acad. Sci.* (*USA*) (1987) 84:2708-2712; and *J. Biol. Chem.* (1987) 262:1030-1036) (1987), as described above.

Despite the fact that yeast NMT recognizes human A-protein as a substrate, the use of yeast-derived protein should be preceded by allergy sensitivity screening and toxicity testing. Immune tolerance to a yeast-derived pharmaceutical may be induced through appropriate immunotherapy, oral or injected (see, e.g., Roitt et al. (eds.) *Immunology* (1993) Mosby-Year Book Europe, London Sec. 10.7). In this regard, care must be taken not to disable elements of the natural anti-tumor response such as T and B-cells and macrophages that are required for successful removal of neoplastic tissues.

Alternatively, to minimize the potential for allergic reactions to non-human proteins, it may be desirable to use human NMT. The methods of Duronio et al. (*Proc. Natl. Acad. Sci.* (*USA*) (1992) 89:4129-4133) may be used to clone NMT from a human genomic library. Human NMT (NMT, EC 2.3.1.97.) is a product of a single copy gene containing 416 amino acids, whose sequence is known (Duronio (1992) ibid.). Briefly, nmt1-181 strain YB207 (Duronio et al. (1991) *J. Cell Biol.* 113:1313-1330) is grown in YPD at 24° C. to a density of $5 \times 10^7$ cells/ml. Spheroplasts are prepared and transformed according to the method of Hinnen et al. (*Proc. Natl. Acad. Sci.* (*USA*) (1978) 75:1929-1932) with a 2.5 μg of library DNA (Schild et al. (1990) *Proc. Natl. Acad. Sci.* (*USA*) 87:2916-2920) and 40 μg of sonicated herring sperm carrier DNA per $10^8$-$10^9$ cells per plate. Ura plates are incubated for 6-7 days at 38° C. Colonies that grow under these conditions are replica-plated to 5-fluoroorotic acid (5-FOA) medium (Boeke et al. (1984) *Mol. Gen. Genet.* 197:345-346) and grown at 24 or 36° C. for 2-3 days. Isolates that grow on 5-FOA at 36° C. are discarded. Isolates that grow only at 24° C. are subcloned into *E. coli* and the plasmid DNA is extracted. The sequence of the DNA is determined by the dideoxynucleotide chain-termination method (Sanger et al. (1977) *Proc. Nat. Acad. Sci.* (*USA*) 74:5463-5467) which may be performed using a commercially available kit such as the Sequenase 2.0 kit (United States Biochemical Corp., Cleveland, Ohio). Plasmids corresponding to the desired sequence of NMT are selected. The plasmids are then subcloned into *E. coli* for expression of the desired protein. NMT is then isolated from *E. coli* according to the methods of Towler et al. (*Proc. Natl. Acad. Sci.* (USA) (1987) 84:2708-2712; and *J. Biol. Chem.* (1987) 262:1030-1036) as described above.

NMT produced for human administration is frozen immediately after preparation and aliquoted in amounts comparable to single dosages. The solution are kept frozen until administered to minimize loss of biological activity.

In some embodiments, the NMT is embedded in a stable biopolymer for slow release. For example, the pharmaceutical composition of the invention may be incorporated into slow release vehicle such as a liposome. Other biopolymers useful as slow release vehicles include acrylic resins, polystyrene microbeads, collagen, polyanhydrides, and other biodegradable matrices known in the art. Other slow release formulations may contain, in addition to other pharmaceutically acceptable carriers, amphipathic agents such as lipids which exist in aggregated form as micelles, insoluble monolayer, liquid crystals, or lamellar layers which are in aqueous solution. Suitable lipids for liposomal formulation include, without limitation, monoglycerides, diglycerides, sulfatides, lysolecithin, phospholipid, saponin, bile acids, and the like. Preparation of such liposomal formulations is within the level of skill in the art, as disclosed, for example, in U.S. Pat. Nos. 4,235,871; 4,501,728; 4,837,028; and 4,737,323. The pharmaceutical composition of the invention may further include other lipid carriers, such as Lipofectamine.

In one therapeutic composition of the invention, myristic acid, NMT, or myristic acid and NMT are combined with a physiologically acceptable carrier. When combined, NMT may complex to CoA via a thioester linkage and hydrophobic interactions. The characteristics of the carrier will depend on the route of administration to be used.

The therapeutic compositions of the invention may contain, in addition to the NMT and/or myristoylCoA and carrier, diluents, fillers, salts, buffers, stabilizers, solubilizers, and other materials well known in the art. The pharmaceutical composition of the invention may also contain other active factors and/or agents which stimulate an immune response to A-protein displaying cells. The pharmaceutical composition of the invention may further contain other chemotherapeutic drugs for the treatment of cancer, such as colony stimulating factors (e.g., GM-CSF). Such additional factors and/or agents may be included in the pharmaceutical composition to produce a synergistic effect with NMT and myristoylCoA, or to minimize side-effects, if any, caused by NMT and/or myristoylCoA.

The therapeutic composition of the invention may be administered in accordance with the method of the invention either alone or in combination with other known therapies for cancer. When co-administered with one or more other therapies, the therapeutic of the invention may be administered either simultaneously with the other treatment(s), or sequentially. If administered sequentially, the attending physician will decide on the appropriate sequence of administering the therapeutic formulations of the invention in combination with the other therapy.

Administration of the therapeutic pharmaceutical composition can be carried out in a variety of conventional ways, such as by intraocular administration, oral ingestion, enteral administration, inhalation, or cutaneous, subcutaneous, intramuscular, or intravenous injection. Sometimes, the pharmaceutical formulation is infused into the circulatory system of the subject via injection.

When a therapeutically effective amount of the therapeutic composition of the invention is administered orally, the therapeutic composition will be in the form of a tablet, capsule, powder, solution or elixir. When administered in tablet form, the therapeutic composition of the invention may additionally contain a solid carrier such as a gelatin or an adjuvant. The tablet, capsule, and powder contain from about 5 to 95% NMT, and/or myristoylCoA, and preferably from about 25 to 90% NMT and myristoylCoA. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of NMT, myristoylCoA. Sustained release oral delivery systems and/or enteric coatings for orally administered dosage forms are also contemplated such as those described in U.S. Pat. Nos. 4,704,295, 4,556,552, 4,309,404, and 4,309,406.

When a therapeutically effective amount of the therapeutic composition of the invention is administered by intravenous, cutaneous, or subcutaneous injection, NMT, myristoylCoA will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to NMT and/or, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of NMT, and/or myristoylCoA in the pharmaceutical composition of the present invention will depend upon the nature and severity of the condition being treated, and on the nature of prior treatments which the patient has undergone. Ultimately, the attending physician will decide the amount of therapeutic composition with which to treat each individual patient. Initially, the attending physician will administer low doses of the therapeutic composition and observe the patient's response. Larger doses may be administered until the optimal therapeutic effect is obtained for the patient, and at that point the dosage is not increased further. The dosages are to be calculated according to the amount of A-protein in the blood of the patient, believed to vary from 5-60 ng/ml of serum, the in vivo rate of myristoylation and the determined in vivo half-life of the NMT. It is contemplated that the various pharmaceutical compositions used to practice the method of the present invention should be administered of about 150 µg to about 500 µg of NMT, and/or myristoylCoA per kg body weight of the subject being treated.

The pharmaceutical formulation can be administered in bolus, continuous, or intermittent dosages, or in a combination of continuous and intermittent dosages, as determined by the physician and the degree and/or stage of illness of the patient. The duration of intravenous therapy using the pharmaceutical composition of the present invention will vary, depending on the severity of the cancer being treated and the condition and potential idiosyncratic response of each individual patient. Ultimately the attending physician will decide on the appropriate duration of intravenous therapy using the pharmaceutical composition of the present invention.

Preferably, the pharmaceutical formulation is infused into the circulatory system of a subject afflicted with cancer. Treatment of the malignant tissue is partially or wholly accomplished by systemic treatment owing to the highly vascular nature of tumor tissue. However, in addition to systemic treatment, patients may benefit from local administration of therapeutic formulations, particularly in instances when anatomical considerations, such as enclosure of the tumor in an organ (eg. prostate, kidney, pancreas, spleen) or accessibility (eg. skin, bladder, cervix, throat) make such treatment feasible and/or desirable.

Therapeutic formulations can be contained at the site of the tumor by injection into the interstitium of an enclosed organ or anatomical space or through surface contact with accessible tumor tissue. Surface contact can be accomplished through lavage of a hollow body space or abdomen or direct placement of the therapeutic on tissues. The NMT and myristoylCoA should be in an appropriately stabilized form that allows for maximum local exposure and minimum escape into other body compartments. It may be useful to utilize impregnated biopolymers for slow release of drugs. In the case of direct application, stabilizing substances such as creams, lotions, or liposomes may be useful.

This is accomplished in several ways depending on the location of the affected tissue.

Since the tumor is the source of A-protein and the site of A-protein displayed as surface antigen, higher concentrations of NMT and myristoylCoA in the immediate vicinity of the tumor are desirable. Local administration also lowers the systemic dosages requireod.

In another aspect, a method of treating a subject with carcinoma is provided as an accompanying therapy. In this method, an immunologically active APC, such as a bone marrow stem cell-derived dendritic cell or a (non-B or non-T type) leukocyte is isolated from the subject. The method of Hsu et al. (*Nature Med*. (1996) 2:52-58), for example, can be used to isolate dendritic cells from the peripheral blood of the patient by leukapheresis. Briefly, mononuclear cells are collected by separation through a Ficoll gradient (Pharmacia, Uppsala, Sweden). Monocytes are removed through a discontinuous Percoll gradient (Pharmacia, Uppsala, Sweden). The mononuclear cells are incubated for 24 hours in medium containing autologous serum and the desired antigen, in this case, myristoylated A-protein or an N-terminal fragment thereof (1-5 µg/ml). Following culture, dendritic cells were separated from high density lymphocytes by centrifugation through metrizamide gradients, after which the enriched dendritic cells are again cultured for 14-18 hours in media containing the antigen (50 µg/ml). The purity of the preparations should be between 50% and 90% dendritic cells as determined by morphology. Following the final incubation, the cells are washed free of excess antigen and resuspended in saline with 5% autologous serum. Between 2 to 32, $10_6$ treated cells may be collected in this manner.

The isolated APC is then then "sensitized" by contact with a peptide that includes an amino terminal sequence of Gly-Asn-Ser-Lys-Ser (SEQ ID NO: 2) to which a myristoyl group is attached at the glycine end. This peptide can be produced synthetically by linking the appropriate amino acids together in step-wise fashion with peptide linkages. In principle, peptide synthesis involves linking an amino acid to a solid matrix support and sequentially linking amino acids in the desired order. The column is washed between steps with the solvent. Finally, the peptide is cleaved from the resin with trifluoroacetic acid and the peptide is harvested and evaporated to a dry powder. This procedure may be performed on a fully automated device (e.g., Millipore 9050 Plus PepSynthesizer).

Alternatively, the APC is sensitized by contact with a homopolymer of the acylated form of A-protein. Acylated A-protein may be isolated from a mammalian species, such as bovine or human A-protein. For example, A-protein can be isolated from the retinas of cow eyes essentially as described by Schmidt et al. (*J. Biol Chem*. (1978) 262:14333-14336). Cow eyes obtained from a local abbatoire within an hour of killing and enucleation are kept on ice in the dark for 1 to 1 ½ hours. Retinas are dissected away from the pigment epithelium of dark-adapted eyes, removed, and placed in Buffer A (100 mM NaC1, 2 mM $MgC1_2$, 20 mM Tris, pH 7.2) at 0.5 ml/retina on ice. Gentle shaking of the vessel results in the liberation of large numbers of rod outer segments (ROS), broken off at the ciliary constriction, into the buffer. The mixture is poured through a ceramic Buchler funnel to remove the retinas. The resulting ROS suspension is sedimented on ice for 5 minutes to allow any gross particulate matter to settle out.

To remove any remaining non-ROS contamination, the ROS suspension is spun down at 5,000 rpm in a refrigerated centrifuge for 10 minutes and the supernatant poured off. The ROS pellet is resuspended in an equal volume of Buffer A by drawing the buffer and ROS repeatedly through a 21-gauge hypodermic needle. This procedure mechanically disrupts the outer segments, and allows soluble ROS constituents to be solubilized in the suspension buffer. Membranes are again spun down in a refrigerated centrifuge at 13,000 rpm for 10 minutes and the supernatant, containing soluble ROS proteins, is removed. The protein solution is placed in an ultrifiltration device (Centricon 30, Amicon Corp., Beverly, Mass.) which retains proteins over an approximate molecular weight of 30 kD. It is then centrifuged at 6,500 rpm in a fixed-angle rotor at 0° C. Because A-protein passes through the filter upon centrifugation, it is rapidly separated from most (>85%) of the other extracted soluble proteins. The ultrafiltrate containing the enriched A-protein fraction is collected upon completion of the run and placed in an ultrifiltration device (Centricon 10, Beverly, Mass.) where the retained proteins are concentrated and dialyzed into Buffer B (20 mM Tris, pH 7.2, 0.1% polyoxyethelyne 23-laurel ether (Brij 35) by centrifugation at 6,500 rpm at 0° C.

The concentrated protein sample is applied to a Sephadex G-50 (Pharmacia, Upsala, Sweden) gel filtration column (2×40 cm) equilibrated with Buffer B. Running time for this column at 0-4° C. is approximately 40 minutes (flow rate of 2 ml/min, 2 ml fractions collected). The A-protein peak is pooled and concentrated by centrifugation.

Alternatively, homopolymers of A-protein may also be cloned from a human genomic or retinal library according to the methods of Dizhoor et al. (*J. Biol. Chem.* (1992) 267: 16033-16036). Briefly this entails constructing oligonucleotide probes that are complementary to portions of the cDNA sequence of A-protein, which is known (Polans et al. (1991) *J. Biol. Chem.* 112:981-989). The library is expanded by polymerase chain reaction and expressed in a host vector such as *E. coli* which has the human DNA subcloned into its chromosomes. Bacteria are grown in culture dishes and the plaques are screened with the positive plaques are selected and rescreened two more times. The gene product of selected plaques is checked for the correct sequence, corresponding to that of A-protein.

A-protein may instead be cloned from a human genomic or retinal library according to the method of Ray et al. (*Proc. Natl. Acad. Sci. (USA)* (1992) 89:5705-5709). Briefly, this entails constructing oligonucleotide probes that are complementary to portions of the cDNA sequence of A-protein. The library is expanded by polymerase chain reaction and expressed in a host vector such as *E. coli* which has the human DNA subcloned into it's chromosomes. Bacteria are grown in culture dishes and the plaques are screened with the oligonucleotide probes. Positive plaques are selected and rescreened two more times. The gene product of selected plaques is checked for the correct sequence, corresponding to that of A-protein.

In addition, the entire gene that codes for A-protein can be wholly synthesized since the cDNA sequence for the gene is known (Polans et al. (1991) *J. Biol. Chem.* 112:981-989). The method of stepwise elongation of sequence may be used to produce a full-length copy of the desired gene (Majumder (1992) *Gene* 10:89-94). Briefly, following the automated production of oligodeoxynucleotides corresponding to the entire sequence of the double stranded gene, the ends of each segment are linked to suitable extension and termination primers. The material thus produced may be expanded by polymerase chain reaction. The oligodeoxynucleotides are joined by adding them to the reaction buffer sequentially in the order in which they are to be joined. The primers allow the segments to self-assemble, forming the double-stranded gene.

The sequence of genes made in this manner are confirmed by automatic sequencing. The A-protein may then be expressed in either a bacterial or viral vector following the inclusion of an appropriate endonuclease site in the untranslated initiator portion of the gene.

A synthetically produced A-protein gene can be expanded through the use of the polymerase chain reaction. These genes may be fashioned into plasmids and subcloned into *E. coli* for fermentation. A-protein produced in this manner is purified from the fermentation media. Viruses such as bacculovirus may also be used as vectors for the expression of A-protein.

The peptide is then spontaneously myristolated in the presence of myristoylCoA, NMT, 150 mM NaCl, 10 NaCl, 10 mM Tris, 2 mM PMSF, pH 7.7 and 0.05% Tween or Triton X-100 at 37° C. The reaction is stopped by lowering the pH to 6.0.

Sensitization of the APC is accomplished by contacting the APC with 2 µg/ml myristoylated peptide or A-protein homopolymer described above in RPMI 1640 and 10% autologous serum at 37° C. with 10% $CO_2$ in an incubator for 24 hours.

The sensitized APC is then reintroduced or administered to the patient to stimulate a T-cell-dependent response against the tumor cells which display the same antigen. In one preferred embodiment, reintroduction is performed by intravenous injection.

In another aspect, the above method of treating a subject with carcinoma is provided as a stand alone therapy. In this method, an APC is isolated from the subject and sensitized to A-protein by contacting the APC with a homopolymer of acylated A-protein. The sensitized APC is then administered to the mammal, thereby stimulating a T-cell-dependent response against the carcinoma.

The present invention also provides kits for treating cancer and for reducing in vivo tolerance to neoplastic tissue. The kit may also be used to produce immune sera in healthy humans which may then be used to treat a subject with carcinoma. Such a kit includes NMT and myristoylCoA as described herein in predetermined amounts. The kit of the invention may optionally include buffers, pharmaceutically acceptable carriers, preparation tools, vials, and the like.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method of stimulating the immune system of a mammal afflicted with an A-protein displaying carcinoma to produce an immune response thereto, the mammal having a detectable blood level of unacylated A-protein, the method comprising the steps of:
   (a) isolating an immunologically active antigen presenting cell (APC) from the mammal;
   (b) sensitizing the APC to A-protein by contacting the APC with a compound selected from the group consisting of an acylated peptide comprising a peptide having at least 10 amino acids including the amino terminal amino acid sequence SEQ ID NO:2 with a myristoyl group attached to the glycine residue of the peptide and a homopolymer of acylated A-protein monomers; and
   (c) administering the sensitized APC to the mammal, thereby relieving the immune system of its tolerance to unacylated A-protein and stimulating a T-cell-dependent response against the carcinoma.

2. The method of claim 1 wherein the sensitized APC is administered intravenously.

3. A method of treating an A-protein displaying carcinoma in a mammal comprising the steps of:
   (a) isolating an immunologically active antigen presenting cell (APC) from the mammal;
   (b) sensitizing the APC to the A-protein by contacting the APC with a compound selected from the group consisting of acylated A-protein monomer and an acylated peptide comprising a peptide having at least 10 amino acids including the amino terminal amino acid sequence SEQ ID NO:2; and
   (c) administering the sensitized APC to the malignant cells expressing unacylated A-protein within the mammal, wherein the sensitized APC stimulates a T cell-dependent response against the carcinoma.

4. The method of claim 3 wherein the sensitized APC is administered intravenously.

5. The method of claim 1 or 3 wherein the carcinoma is small cell carcinoma of the lung (SCCL).

6. The method of claim 1 or 3 wherein the antigen presenting cell (APC) is a dendritic cell.

* * * * *